United States Patent
Schwab et al.

(10) Patent No.: US 12,138,335 B2
(45) Date of Patent: *Nov. 12, 2024

(54) OPAQUE COMPOSITION COMPRISING ETHYLENE GLYCOL DISTEARATE

(71) Applicant: Evonik Operations GmbH, Essen (DE)

(72) Inventors: Peter Schwab, Essen (DE); Dominik Schuch, Düsseldorf (DE); Patrick Winter, Mülheim an der Ruhr (DE); Peter Muss, Essen (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/044,049

(22) PCT Filed: Apr. 12, 2019

(86) PCT No.: PCT/EP2019/059463
§ 371 (c)(1),
(2) Date: Sep. 30, 2020

(87) PCT Pub. No.: WO2019/197626
PCT Pub. Date: Oct. 17, 2019

(65) Prior Publication Data
US 2021/0154115 A1     May 27, 2021

(30) Foreign Application Priority Data

Apr. 13, 2018  (EP) .................................. 18167225

(51) Int. Cl.
| | | |
|---|---|---|
| *A61K 8/37* | (2006.01) | |
| *A61K 8/46* | (2006.01) | |
| *A61Q 5/02* | (2006.01) | |
| *A61Q 19/10* | (2006.01) | |

(52) U.S. Cl.
CPC .............. *A61K 8/375* (2013.01); *A61K 8/463* (2013.01); *A61Q 5/02* (2013.01); *A61Q 19/10* (2013.01); *A61K 2800/26* (2013.01); *A61K 2800/30* (2013.01); *A61K 2800/805* (2013.01)

(58) Field of Classification Search
None
See application file for complete search history.

(56) References Cited

U.S. PATENT DOCUMENTS

| | | |
|---|---|---|
| 9,776,951 B2 | 10/2017 | Friedrich et al. |
| 9,890,107 B2 | 2/2018 | Schuch et al. |
| 10,370,493 B2 | 8/2019 | Brandt et al. |
| 10,618,867 B2 | 4/2020 | Liebig et al. |
| 2004/0037793 A1 | 2/2004 | Nieendick et al. |
| 2016/0022566 A1* | 1/2016 | Figura .................... A61K 8/898 510/125 |
| 2018/0110718 A1* | 4/2018 | Hloucha ................. A61K 8/922 |
| 2018/0344602 A1 | 12/2018 | Schuch et al. |
| 2020/0155436 A1 | 5/2020 | Hartung et al. |
| 2021/0069077 A1 | 3/2021 | Schwab et al. |

FOREIGN PATENT DOCUMENTS

| | | |
|---|---|---|
| DE | 19801231 C1 | 4/1999 |
| EP | 0563343 | 10/1993 |
| EP | 0568848 A1 | 11/1993 |
| JP | 2003055165 | 2/2003 |

OTHER PUBLICATIONS

Shimada et al. English translation of JP 2003/055165 A (Year: 2003).*
Paula's Choice "Skin Care Ingredient Dictionary" <https://www.paulaschoice.com/ingredient-dictionary?crefn1=ingredientNameFirstCharacter&crefv1=L&crefn2=ingredientRating&crefv2=Good&csortb1=name&csortd1=1&start=10&sz=10> accessed Apr. 25, 2024 (Year: 2023).*
Brandt et al., U.S. Appl. No. 16/857,523, filed Apr. 24, 2020.
English International Search Report mailed on Jun. 3, 2019 in PCT/EP2019/059463 (2 pages).
German International Search Report mailed on Jun. 3, 2019 in PCT/EP2019/059463 (4 pages).
Schwab et al., U.S. Appl. No. 16/993,428, filed Aug. 14, 2020.
Written Opinion mailed on Jun. 3, 2019 in PCT/EP2019/059463 (9 pages).
U.S. Office Action dated May 26, 2022, in U.S. Appl. No. 16/993,428, 9 pages.
U.S. Appl. No. 16/993,428, filed Aug. 14, 2020, 2021/0069077, Schwab et al.

* cited by examiner

*Primary Examiner* — Nicole P Babson
(74) *Attorney, Agent, or Firm* — Grüneberg and Myers PLLC

(57) ABSTRACT

A process for preparing an opaque composition using ethylene glycol distearate including the steps of providing a starting composition including A) from 0.5 parts by weight to 15 parts by weight of at least one surfactant, B) from 0.5 parts by weight to 15 parts by weight of at least one emulsifier, C) from 10 parts by weight to 30 parts by weight ethylene glycol distearate, and D) from 20 parts by weight to 85 parts by weight water; b) stirring the starting composition at a temperature in a range from 60° C. to 100° C.; and c) cooling to a temperature in a range from 5° C. to 55° C. to obtain the opaque composition.

14 Claims, 2 Drawing Sheets

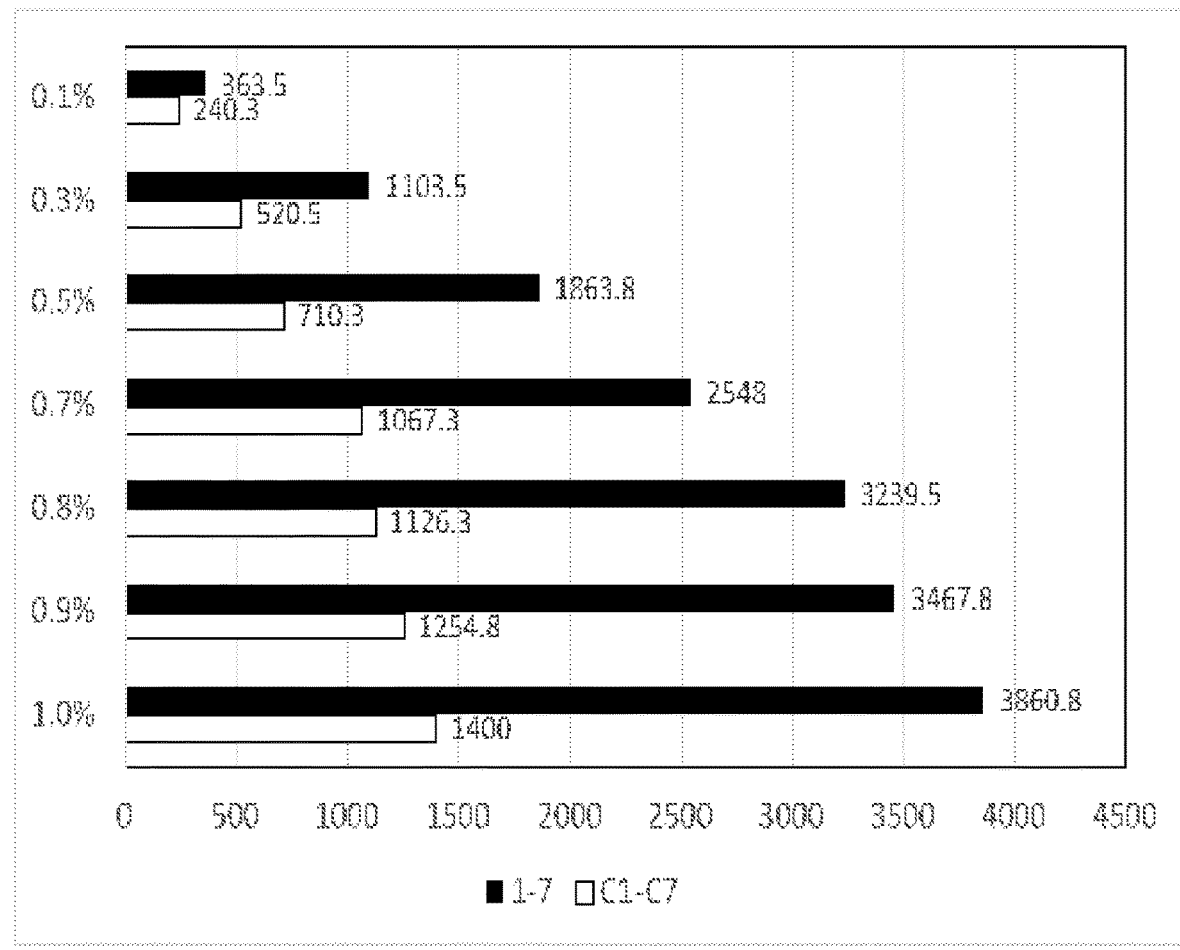
Figure 1: Turbidity values of inventive formulations 1-7 and comparative formulations C1-C7

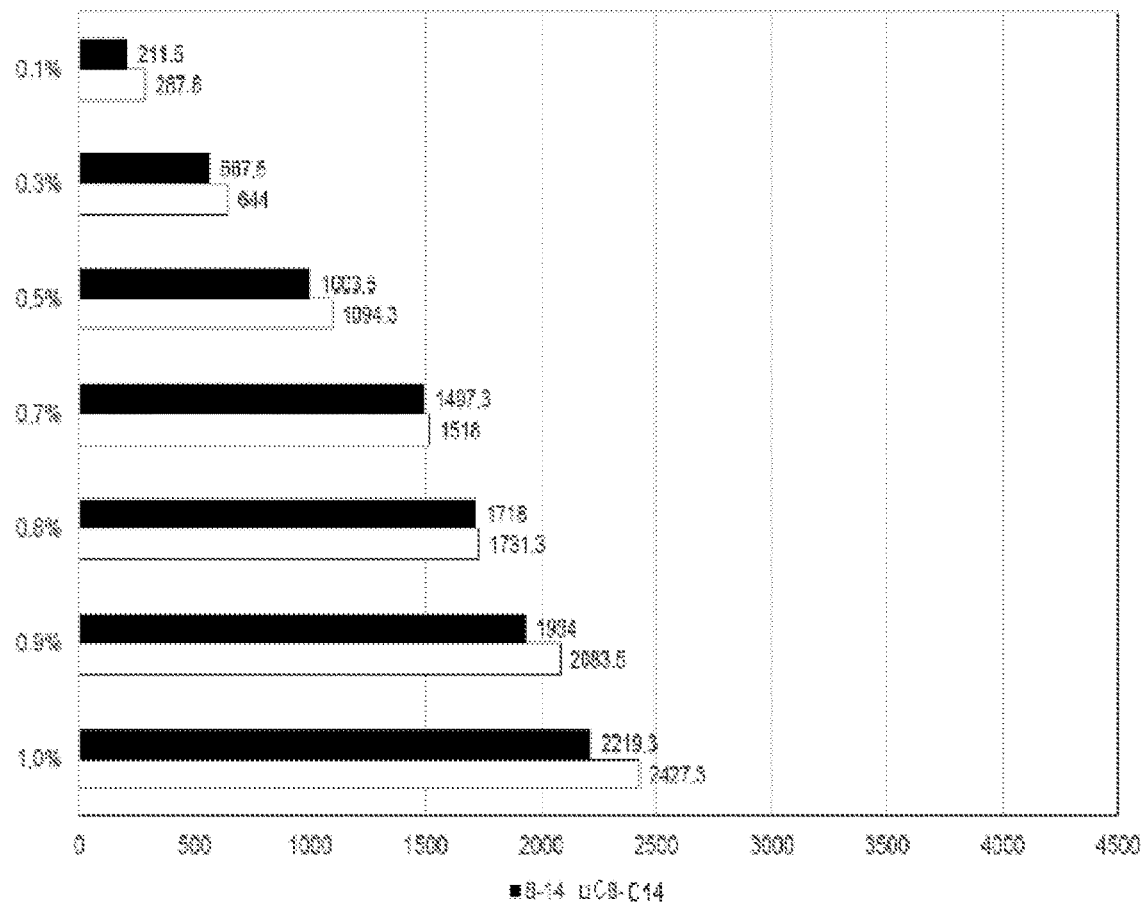
Figure 2: Turbidity values of the inventive opaque composition diluted in water according to example 1 (8-14) and of the market standard styrene/acrylates copolymer (C8-C14).

OPAQUE COMPOSITION COMPRISING ETHYLENE GLYCOL DISTEARATE

CROSS REFERENCE TO RELATED APPLICATIONS

This application is a 35 U.S.C. § 371 U.S. national phase entry of International Application No. PCT/EP2019/059463 having an international filing date of Apr. 12, 2019, which claims the benefit of European Application No. 18167225.4 filed Apr. 13, 2018, each of which is incorporated herein by reference in its entirety.

FIELD

The invention relates to a process for preparing an opaque composition using ethylene glycol distearate.

BACKGROUND

Ethylene glycol distearate (EGDS) has long been used for achieving pearlescent effects in formulations. For cosmetic formulations, this pearlizer is sold under the INCI name glycol distearate for example.

For instance, CN192816613 describes the preparation of pearlescent ethylene glycol distearate in an aqueous medium with a surface-active substance with heating and cooling and subsequent pH adjustment. The pearlescent ethylene glycol distearate is also used in low-water-content car wash formulations.

JP2003055165 discloses opacifiers composed of fatty acid glycol esters and surfactants. Due to the ongoing discussion about microplastics in cosmetic products, manufacturers are looking for alternatives to the styrene-acrylate copolymers (styrene/acrylates copolymer) used as opacifier.

SUMMARY

It has been found that, surprisingly, ethylene glycol distearate-containing compositions, prepared by a novel process, may be used as alternative opacifiers. The ethylene glycol distearate compositions described in the present invention are generally characterized by a reduced pearlescent effect compared to conventional ethylene glycol distearate compositions.

It was an object of the invention to provide replacement substances for opacifiers based on styrene-acrylate copolymers.

DETAILED DESCRIPTION

The present invention therefore provides a process for preparing a composition comprising ethylene glycol distearate as described in Claim 1.

The invention further provides certain opaque compositions comprising ethylene glycol distearate which may be used as opacifiers, and also opaque formulations comprising the opaque compositions according to the invention.

An advantage of the present invention is that the opaque compositions, at comparable use concentration in formulations, produce a comparable whiteness and a comparable, preferably improved turbidity value in relation to the conventional styrene-acrylate copolymers.

A further advantage of the present invention is that the opaque compositions are not highly viscous and therefore can be easily pumped.

Another advantage of the present invention is that the constituents of the composition are readily biodegradable.

A further advantage of the present invention is that the composition, in a particular embodiment, is free of polyethylene glycol constituents.

A further advantage of the present invention is the high degree of whiteness of the opacifiers.

A further advantage of the present invention is that the degree of whiteness does not change on storage.

Another advantage of the present invention is the low particle size of the opacifiers.

A further advantage of the present invention is the low abrasion effect of the opacifiers associated with a good soft skin feel.

A further advantage of the present invention is the good compatibility of the opacifiers with other formulation components, which prevents agglomeration.

Another advantage of the present invention is the good dispersibility of the opacifiers.

A further advantage of the present invention is the low solubility of the opacifiers in many solvents, particularly in formulations suitable for cosmetic purposes.

Yet another advantage of the present invention is the outstanding opacity, measured by fineness and refractive index of the opacifiers.

In the present case, therefore, what is claimed is a process for preparing an opaque composition which preferably has no pearlescent effect, comprising the steps of
a) providing a starting composition comprising
A) 0.5 parts by weight to 15 parts by weight, preferably 3 parts by weight to 15 parts by weight, of at least one surfactant,
B) 0.5 parts by weight to 15 parts by weight, preferably 3 parts by weight to 15 parts by weight, of at least one emulsifier,
C) 10 parts by weight to 30 parts by weight ethylene glycol distearate,
D) 20 parts by weight to 85 parts by weight water,
b) stirring the starting composition at a temperature in a range from 60° C. to 100° C., preferably 65° C. to 95° C. and particularly preferably 70° C. to 90° C.,
c) cooling to a temperature in a range from 5° C. to 55° C., preferably 10° C. to 50° C., particularly preferably 15° C. to 45° C. to obtain the opaque composition.

The specified parts by weight refer in each case to the total amount of all individual surfactants or individual emulsifiers.

In contrast to transparent materials are materials referred to as translucent or transparent, which allow light to pass through but behind which, as in the case of frosted glass, no items are recognizable. In the case of materials impervious to light in contrast, this is referred to as opacity. Opacity is a measure of the opaqueness (turbidity) of substances and is the reciprocal of translucence. Opacity is the reciprocal of transmission.

In the context of the present invention, the term "opaque" is consequently understood to mean compositions which are cloudy to a certain degree.

The cloudiness, also turbidity (lat. turbidus, 'cloudy'), of a liquid is caused by small particles which have a refractive index different from the carrier substance or cause absorption. Nowadays, the turbidity of a liquid is determined optically and measured by means of electronic evaluation. The wavelength of the measuring radiation is typically in the infrared region at 860 nm (according to ISO 7027).

Generally two measuring methods are distinguished: attenuation of the light radiation passing through (transmitted light), most suitable for detection of dense turbidity.

Sideward scattering of the light radiation (scattered light), most suitable for detection of weak turbidity.

In order to be able to measure turbidity in a manner that allows comparison, the turbidity standard liquid formazin was employed. All turbidity units refer to dilutions of this liquid.

The most commonly used turbidity units are:

FAU Formazin Attenuation Units—measurement of transmitted light (angle 0°) according to the specifications of the standard ISO 7027

FNU Formazin Nephelometric Units—measurement of scattered light (angle 90°) according to the specifications of the standard ISO 7027

FTU Formazin Turbidity Unit—the unit used in water treatment

In the context of the present invention, the term "opaque" is consequently understood to mean compositions having a turbidity value of 500 Formazin Nephelometric Units or more. The Formazin Nephelometric Units abbreviated as FNU in the context of the present invention are determined by a scattered light measurement, such as conducted in the examples of the present document.

In the context of the present invention, the expression "having no pearlescent effect" or "having no pearlescent properties" is understood to mean that the opaque composition according to the invention in question, in the form of an aqueous composition diluted to 3 percent by weight, where the percentages by weight are based on the overall aqueous composition, has a luminance of not less than 187. Such high luminance values cannot be achieved by pearlescent compositions owing to light scatter that occurs.

Luminance is ascertained in the context of the present invention as conducted in the examples of the present document.

In the context of the present invention, the terms "surfactant" and "emulsifier" are understood to mean organic substances having interface-active properties that have the ability to reduce the surface tension of water at 20° C. and at a concentration of 0.5% by weight based on the overall composition to below 45 mN/m. Surfactants have positively and/or negatively charged functional groups in their chemical structural formula, whereas emulsifiers, with regard to their chemical structural formula, do not contain any charged functional groups, considered within a pH range from 2 to 12 and at a temperature of 20° C.

Surface tension is determined by the DuNoüy ring method at 20° C.

Consequently, in the context of the present invention, emulsifiers and surfactants can be unambiguously separated from one another and do not overlap.

"pH" in the context of the present invention is defined as the value which is measured for the corresponding composition at 20° C. after stirring for five minutes by a pH electrode calibrated according to ISO 4319 (1977).

Unless stated otherwise, all percentages (%) given are percentages by mass.

In the process according to the invention, it is preferred that components A), B), C) and D) in total amount to at least 66% by weight, preferably at least 90% by weight, based on the composition obtained by the process according to the invention.

In the process of the present invention, the at least one surfactant in component A) is preferably selected from the group consisting of anionic and amphoteric surfactants comprising at least one nitrogen atom or one sulfur atom, preferably amphoacetates, amphopropionates and optionally alkoxylated, in particular optionally ethoxylated, sulfosuccinates, particularly preferably sulfosuccinates derived from monoesters, especially disodium laureth sulfosuccinate, disodium lauryl sulfosuccinate, and also sodium lauryl ether sulfate, also known as sodium laureth sulfate (SLES), and also betaines, alkyl- and amidopropylbetaines, especially cocamidopropylbetaine (CAPB).

It is advantageous when, in the process of the present invention, component A) is optionally alkoxylated, especially optionally ethoxylated, sulfosuccinates, more preferably monoester-derived sulfosuccinates, especially Disodium Laureth Sulfosuccinate or Disodium Lauryl Sulfosuccinate. This has the technical effect that compositions having a low viscosity and simultaneously high turbidity are obtained. These compositions thus have good pumpability and hence can be processed more easily. In formulations, it is possible to produce high turbidity levels with avoidance of pearlescent effects.

It is especially advantageous when, in the process of the present invention, component A) is a mixture of sodium lauryl ether sulfate and/or optionally ethoxylated sulfosuccinate, especially sodium lauryl ether sulfate, with betaine, especially cocamidopropyl betaine, preferably in a weight ratio of sodium lauryl ether sulfate and/or optionally ethoxylated sulfosuccinate to betaine of 15:1 to 1:2.

A preferred process according to the invention is characterized in that the at least one emulsifier in component B) is selected from the group consisting of alkoxylates and also fatty acid esters and glycosides, particularly preferably alkoxylated, especially ethoxylated, fatty alcohols, methyl glucose fatty acid esters, sorbitan fatty acid esters, glycerol fatty acid esters and polyglycerol fatty acid esters or mixed esters thereof.

Preferred ethoxylated fatty alcohols are selected from ethoxylated fatty alcohols having a chain length of 8 to 16 carbon atoms, especially ethoxylated lauryl alcohol, especially Laureth-4. Preferred glycerol fatty acid esters are selected from glycerol esters of fatty acids selected from fatty acids having a chain length of 8 to 22 carbon atoms, especially having a degree of esterification averaging 0.7 to 1.5 fatty acid residues per glycerol fatty acid ester. In particular, such glycerol fatty acid esters are selected from glyceryl laurate and glyceryl oleate.

Preferred polyglycerol fatty acid esters are selected from those having an average degree of polymerization of the polyglycerol of 2.5 to 10, having a degree of esterification averaging 0.5 to 2.0 fatty acid residues per polyglycerol fatty acid ester and having a fatty acid selected from fatty acids having a chain length of 8 to 22 carbon atoms.

The degree of polymerization n can be determined by ascertaining the hydroxyl number of the polyglycerol used for the synthesis of the ester of the invention, where the average degree of polymerization n is linked to the hydroxyl number of the parent polyglycerol via the following equation:

$$n = \frac{\frac{2000 \cdot M(\text{KOH})}{OHN} - M(\text{water})}{\left[[M(\text{glycerol}) - M(\text{water})] - \frac{1000 \cdot M(\text{KOH})}{OHN}\right]}$$

with M=molar mass; OHN=hydroxyl number of the free polyglycerol.

Alternatively, the degree of polymerization n can also be determined by ascertaining the hydroxyl number of the polyglycerol obtained after complete ester hydrolysis.

Suitable determination methods for ascertaining the hydroxyl number are especially those according to DGF C-V 17 a (53), Ph. Eur. 2.5.3 Method A and DIN 53240.

In a process particularly preferred in accordance with the invention, component A) is selected from a mixture of sodium lauryl ether sulfate with betaine, preferably in a weight ratio of 12:1 to 1:1, and component B) is selected from glycerol fatty acid esters, especially glyceryl oleate. This has the technical effect that compositions having particularly good storage stability and very high turbidity are obtained, which do not produce any pearlescent effect in formulations.

In a process which is alternatively particularly preferred in accordance with the invention, component A) is selected from ethoxylated sulfosuccinate and component B) is selected from ethoxylated fatty alcohols, especially ethoxylated lauryl alcohol, especially Laureth-4.

In a preferred embodiment, the process according to the invention is one for production of an opaque composition which is essentially free of polyethers and polyether-containing compounds and preferably has no pearlescence.

Thus, all components used in this preferred embodiment of the process according to the invention are essentially free of polyethers and polyether-containing compounds.

In the context of the present invention, what is meant by the expression "essentially free of polyethers and polyether-containing compounds" is that compounds present contain only traces of, preferably no, alkoxy groups, oligoalkoxy groups or polyalkoxy groups, for example ethylene oxide or propylene oxide. The concentration of polyether-containing compounds should be less than 0.1% by weight, especially preferably less than 0.01% by weight, based on the overall formulation, preferably below the detection limit of standard analysis methods, for example GC, HPLC, NMR spectroscopy, GPC or Maldi.

In this preferred embodiment of the process according to the invention, component A) used with preference is selected from sulfosuccinates, preferably from monoester-derived sulfosuccinates, for example Disodium Lauryl Sulfosuccinate, Disodium Undecylenamido MEA Sulfosuccinate, Disodium Ricinoleamido MEA Sulfosuccinate, Diethylhexyl Sodium Sulfosuccinate, Disodium Cocamide MEA Sulfosuccinate, Ammonium Dinonyl Sulfosuccinate, Ammonium Lauryl Sulfosuccinate, Diammonium Lauramido MEA Sulfosuccinate, Diammonium Lauryl Sulfosuccinate, Diamyl Sodium Sulfosuccinate, Dicapryl Sodium Sulfosuccinate, Dicyclohexyl Sodium Sulfosuccinate, Diheptyl Sodium Sulfosuccinate, Dihexyl Sodium Sulfosuccinate, Diisobutyl Sodium Sulfosuccinate, Diociyl Sodium Sulfosuccinate, Disodium Cetearyl Sulfosuccinate, Disodium Cocamide MEA-Sulfosuccinate, Cocamide MIPA-Sulfosuccinate Disodium, Disodium Coco-Glucoside Sulfosuccinate, Disodium Dihydroxiethyl Sulfosuccinyl Undecilenate, Disodium Hydrogenated Cottonseed Glyceride Sulfosuccinate, Disodium Isodecyl Sulfosuccinate, Disodium Isostearamido MEA-Sulfosuccinate, Disodium Isostearamido MIPA-Sulfosuccinate, Disodium Isostearyl Sulfosuccinate, Disodium Lauramido MEA-Sulfosuccinate, Disodium Myristamido MEA-Sulfosuccinate, Disodium Oleamido MEA Sulfosuccinate, Disodium Oleamido MIPA Sulfosuccinate, Disodium Oleyl Sulfosuccinate, Disodium Ricinoleamido MEA-Sulfosuccimate, Disodium Stearamido MEA-Sulfosuccinate, Disodium Stearyl Sulfosuccinamate, Disodium Stearyl Sulfosuccinate, Disodium Tallamido MEA-Sulfosuccinate, Disodium Tallowamido MEA-Sulfosuccinate, Disodium Tallow Sulfosuccinamate, Disodium Tridecyl Sulfosuccinate, Disodium Wheat Germamido MEA-Sulfosuccinate, Ditridecyl Sodium Sulfosuccinate, Sodium Bisglycol Ricinosulfosuccinate, and component B) is selected from methylglucose fatty acid esters, sorbitan fatty acid esters, glycerol fatty acid esters and polyglycerol fatty acid esters and mixed esters of the above, particular preference being given to the representatives of the glycerol fatty acid esters that have already been mentioned above as preferred.

As component C) it is also possible to use technical grade ethylene glycol distearate as the ethylene glycol distearate, the degree of esterification of which for example is not exactly two ("diester"), but for example is 1.5 (so-called "ethylene glycol sesquistearate"). In addition or as an alternative, for example, some of the stearic acid residues may be substituted by palmitic acid residues.

It is preferable in accordance with the invention that the starting composition of process step a) has a pH of 4 to 7 at 20° C.

It is preferable in accordance with the invention that the stirring in process step b) has a duration of 0.25 to 6.0 hours, preferably 0.5 to 4.0 hours.

A preferred process according to the invention is characterized in that components A) to D) of the starting composition are in the form of a homogeneous emulsion in process step b).

Process step c) of the process according to the invention is preferably carried out at a cooling rate of 0.1° C./min to 15° C./min, preferably 0.2° C./min to 10° C./min, particularly preferably 0.3° C./min to 5° C./min.

In process steps b) and/or c), it is also possible to add additionally component D), water, preferably up to a maximum concentration of 85% by weight, based on the opaque composition.

A preferred process according to the invention is characterized in that in process step c) the cooling is carried out partially by adding water to the starting composition, preferably obtaining an opaque composition having a water content of 50% by weight to 85% by weight water, where the percentages by weight refer to the total composition.

The present invention further provides an opaque composition obtainable by the process according to the invention.

The present invention still further provides an opaque composition comprising

A2) 0.5% by weight to 15% by weight, preferably 3% by weight to 15% by weight, of at least one surfactant,
B2) 0.5% by weight to 15% by weight, preferably 3% by weight to 15% by weight, of at least one emulsifier,
C2) 10% by weight to 30% by weight ethylene glycol distearate,
D2) 50% by weight to 84% by weight water,
where the percentages by weight refer to the total composition.

Preferably according to the invention, the compositions according to the invention comprise components A2), B2), C2) and D2) in a total amount of at least 66% by weight, preferably at least 90% by weight, based on the total composition.

The opaque compositions obtainable by the process according to the invention and the compositions according to the invention preferably have a viscosity of 10 to 30 000 mPa s, particularly preferably a viscosity of 100 to 10 000 mPa s, especially preferably a viscosity of 500, preferably 1000, particularly preferably 1200 to 7000 mPa s, measured at 25° C. with a Brookfield viscometer using RV spindle=5 and at 10 rpm.

The opaque compositions obtainable by the process according to the invention and the opaque compositions according to the invention, at a concentration of 0.3% by weight in water, where the percentages by weight refer to the sum total of water and total formulation, preferably have a turbidity value of 500, preferably 1000, more preferably 1200 or more formazin nephelometric units.

The opaque compositions obtainable by the process according to the invention and the opaque compositions according to the invention differ from those of the prior art in particular in that they have no pearlescent properties.

Preferably, the opaque compositions obtainable by the process according to the invention and the opaque compositions according to the invention, in the form of an aqueous composition diluted to 3 percent by weight, where the percentages by weight are based on the overall aqueous composition, have a luminance of greater than 187, preferably greater than 190.

Components A2), B2), C2) and D2) are preferred in accordance with the weighting of the preference of the respective components A), B), C) and D) of the process according to the invention; the same applies to correspondingly preferred combinations of the components.

The opaque compositions obtainable by the process according to the invention and the opaque compositions according to the invention are thus also preferably essentially free of polyethers and polyether-containing compounds.

The opaque compositions obtainable by the process according to the invention and the opaque compositions according to the invention are of excellent suitability for production of opaque formulations, especially cosmetic formulations, very particularly of cleansing formulations for the skin and/or hair.

These opaque compositions according to the invention can be prepared in a further process according to the invention for preparing opaque formulations, particularly opaque cosmetic formulations, very particularly opaque cleansing formulations for skin and/or hair, which comprises the process steps of:
a) providing a starting composition comprising
  A) 0.5 parts by weight to 15 parts by weight, preferably 3 parts by weight to 15 parts by weight, of at least one surfactant,
  B) 0.5 parts by weight to 15 parts by weight, preferably 3 parts by weight to 15 parts by weight, of at least one emulsifier,
  C) 10 parts by weight to 30 parts by weight ethylene glycol distearate,
  D) 20 parts by weight to 85 parts by weight water,
b) stirring the starting composition at a temperature in a range from 60° C. to 100° C., preferably 65° C. to 95° C. and particularly preferably 70° C. to 90° C.,
c) cooling to a temperature in a range from 5° C. to 55° C., preferably 10° C. to 50° C., particularly preferably 15° C. to 45° C. to obtain the opaque composition,
d) blending the opaque composition with further components in a temperature range from 5° C. to 40° C., preferably 10° C. to 35° C., particularly preferably 15° C. to 25° C., to obtain an opaque formulation.

In this further process according to the invention, the identical preferred embodiments are used in process step a) to c) as described above for the first process according to the invention.

In this further process according to the invention, it is preferred that components A), B), C) and D) amount to a total of at least 0.5% by weight based on the formulation obtained by this further process according to the invention.

The present invention therefore further provides also opaque formulations comprising opaque compositions obtainable by the first process according to the invention and/or compositions according to the invention, preferably in an amount of 0.1% by weight to 15% by weight, particularly preferably 0.5% by weight to 10% by weight, especially preferably 1% by weight to 6% by weight, where the percentages by weight refer to the total formulation.

The opaque formulations according to the invention preferably have a turbidity value of 600, preferably 750, especially 1000 or more formazin nephelometric units.

The opaque formulations according to the invention are preferably characterized in that they have no pearlescent properties.

The present invention further relates to the use of opaque compositions obtainable by the first process according to the invention and/or the opaque compositions according to the invention as opacifiers, particularly without a pearlescent effect being generated in the use according to the invention.

The examples adduced hereinafter describe the present invention by way of example, without any intention that the invention, the scope of application of which is apparent from the entirety of the description and the claims, be restricted to the embodiments specified in the examples.

The following figures are part of the examples:
FIG. 1: Turbidity values of inventive formulations 1-7 and comparative formulation C1-C7
FIG. 2: Turbidity values of the inventive opaque composition diluted in water according to example 1 and of the market standard styrene/acrylates copolymer.

EXAMPLES

In the following, the constituents of the compositions are named in the form of the generally recognized INCI nomenclature using the English terms. The viscosities were measured at 22° C. using a Brookfield viscometer and a spindle 5. The number of revolutions was set at 10 or 100 revolutions per minute depending on the resistance.

Example 1: Preparation of Inventive Opaque Compositions

Example 1.1: Inventive Opaque Composition

A mixture of 5 parts by weight Disodium Laureth Sulfosuccinate, 7 parts by weight Laureth-4, 17 parts by weight Glycol Distearate and 25 parts by weight water was stirred at 80° C. for 0.5 h. The mixture was then cooled to 35° C. over 20 minutes by adding 45 parts by weight water (20° C.).

A white, homogeneous suspension was obtained, which was stored at 22° C. and had a viscosity of 340 mPa s after 24 h and 452 mPa s after 1 week. The suspension did not show any separation effects within 6 weeks.

Example 1.2: Inventive Opaque Composition

A mixture of 6 parts by weight of Sodium Laureth Sulfate, 7 parts by weight of Laureth-4, 16 parts by weight of Glycol Distearate and 37 parts by weight of water was stirred at 80° C. for 0.5 h. Subsequently, with addition of 34 parts by weight of water (20° C.), the mixture was cooled down to 35° C. within 0.5 h.

A white, homogeneous suspension was obtained, which was stored at 22° C. and had a viscosity of 11640 mPa s after 24 h and 16400 mPa s after 1 week. The suspension did not show any separation effects within 6 weeks.

Example 1.3: Inventive Opaque Composition

A mixture of 9 parts by weight of Sodium Laureth Sulfate, 2 parts by weight of Cocamidopropyl Betaine, 1 part by weight of Glyceryl Oleate, 25 parts by weight of Glycol Distearate and 63 parts by weight of water was stirred at 80° C. for 0.5 h. This was followed by cooling to 27° C. within 1.5 h.

A white, homogeneous suspension was obtained, which was stored at 22° C. and had a viscosity of 2600 mPa s after 24 h and 3700 mPa s after 1 week. The suspension did not show any separation effects within 6 weeks.

Example 1.4: Inventive Opaque Composition

A mixture of 6 parts by weight of Disodium Lauryl Sulfosuccinate, 7 parts by weight of Glyceryl Laurate, 17 parts by weight of Glycol Distearate and 24 parts by weight of water was stirred at 80° C. for 0.5 h. Subsequently, the mixture, with addition of 46 parts by weight of water (20° C.), was cooled down to 35° C. within 20 minutes.

A white, homogeneous suspension was obtained, which was stored at 22° C. and, after 24 h, had a viscosity of 30000 mPa s. The suspension did not show any separation effects within 6 weeks.

Example 1.5: Inventive Opaque Composition

A mixture of 6 parts by weight of Disodium Lauryl Sulfosuccinate, 5 parts by weight of Glyceryl Laurate, 17 parts by weight of Glycol Distearate and 39 parts by weight of water was stirred at 80° C. for 0.5 h. Subsequently, the mixture, with addition of 33 parts by weight of water (20° C.), was cooled down to 35° C. within 20 minutes.

A white, homogeneous suspension was obtained, which was stored at 22° C. and, after 24 h, had a viscosity of 1080 mPa s. The suspension did not show any separation effects within 6 weeks.

Example 1.6: Inventive Opaque Composition

A mixture of 6 parts by weight of Disodium Lauryl Sulfosuccinate, 6 parts by weight of Glyceryl Oleate, 17 parts by weight of Glycol Distearate and 39 parts by weight of water was stirred at 80° C. for 0.5 h. Subsequently, the mixture, with addition of 32 parts by weight of water (20° C.), was cooled down to 35° C. within 20 minutes.

A white, homogeneous suspension was obtained, which was stored at 22° C. and, after 24 h, had a viscosity of 2400 mPa s. The suspension did not show any separation effects within 6 weeks.

Example 2: Inventive Opaque Composition

A mixture consisting of 8% by weight Disodium Cocoamphopropionate, 10% by weight Laureth-4, 25% by weight Glycol Distearate and 57% by weight water was stirred at 80° C. for 1 h. The mixture was then cooled to 30° C. over a period of 60 minutes.

Example 3: Determination of the Turbidity Values of Formulations According to the Invention Comprising Inventive Opaque Composition The inventive composition of example 1.1 was homogeneously stirred into a surfactant mixture consisting of 9 parts by weight SLES (Sodium Laureth Sulfate) and 3 parts by weight CAPB (Cocamidopropyl Betaine) according to Table 1 and thickened by adding 1% NaCl:

TABLE 1

Inventive opaque formulations 1-7 prepared from inventive example 1.1

| — | 1 | 2 | 3 | 4 | 5 | 6 | 7 |
|---|---|---|---|---|---|---|---|
| SLES (28% a.m.) | 32 | 32 | 32 | 32 | 32 | 32 | 32 |
| Water | 58.65 | 58.45 | 58.25 | 58.05 | 57.95 | 57.85 | 57.75 |
| TEGO ® Betain F 50 (38% a.m.) | 8 | 8 | 8 | 8 | 8 | 8 | 8 |
| Inventive Example 1.1 | 0.1 | 0.3 | 0.5 | 0.7 | 0.8 | 0.9 | 1 |
| NaCl | 0.8 | 0.8 | 0.8 | 0.8 | 0.8 | 0.8 | 0.8 |
| Neolone PE | 0.45 | 0.45 | 0.45 | 0.45 | 0.45 | 0.45 | 0.45 |
| pH | 5.5 | 5.5 | 5.5 | 5.5 | 5.5 | 5.5 | 5.5 |

For comparison, a benchmark styrene/acrylates copolymer was also stirred homogeneously into the same surfactant mixture and analogously thickened:

TABLE 2

Comparative formulations C1-C7

| — | C1 | C2 | C3 | C4 | C5 | C6 | C7 |
|---|---|---|---|---|---|---|---|
| SLES (28% a.m.) | 32 | 32 | 32 | 32 | 32 | 32 | 32 |
| Water | 58.65 | 58.45 | 58.25 | 58.05 | 57.95 | 57.85 | 57.75 |
| TEGO ® Betain F 50 (38% a.m.) | 8 | 8 | 8 | 8 | 8 | 8 | 8 |
| Acusol OP 301 (17% a.m.) | 0.1 | 0.3 | 0.5 | 0.7 | 0.8 | 0.9 | 1 |
| NaCl | 0.8 | 0.8 | 0.8 | 0.8 | 0.8 | 0.8 | 0.8 |
| Neolone PE | 0.45 | 0.45 | 0.45 | 0.45 | 0.45 | 0.45 | 0.45 |
| pH | 5.5 | 5.5 | 5.5 | 5.5 | 5.5 | 5.5 | 5.5 |

The turbidity values were determined for the inventive opaque formulations 1-7 and the comparative formulations C1-C7. The measuring instrument used was an Iso Turbidity Meter, HI 88713 from Hanna Instruments, which was operated in the measuring mode: "NTU ratio mode". For this purpose, indexed cuvettes were filled up to the 10 mL mark and degassed. The cuvettes were then measured in the measurement cell at room temperature. The cuvette was turned 90° after each measurement. In this way, four measurements in total were taken and the average value then calculated. The measured values are reported in NTU.

The results are shown in FIG. 1. The measured values in FIG. 1 show that the formulations according to the invention have significantly higher turbidity values at the same active content.

Example 4: Turbidity Values of the Inventive Compositions

In a manner analogous to Example 3, the turbidity values of the inventive composition according to Example 1.1 were measured in a dilution series in water.

The results are summarized in FIG. 2: The opaque composition according to the invention shows comparable turbidity values to the market standard styrene/acrylates copolymer.

Analogously to Example 3, the turbidity values of the composition according to the invention as per Examples 1.1 to 2 were measured at a concentration of 0.5% by weight.

Turbidity values, 0.5% in SLES/CAPB:

| | |
|---|---|
| Example 1.1 | 1864 NTU |
| Example 1.2 | 1739 NTU |
| Example 1.3 | 4000 NTU |
| Example 1.4 | 1628 NTU |
| Example 1.5 | 1660 NTU |
| Example 1.6 | 1669 NTU |
| Example 2 | 1350 NTU |

Example 5: Determination of Pearlescent Properties

To determine luminance, 3% of the blends are carefully stirred into a surfactant mixture of SLES/CAPB (11.2:3.8 active matter) thickened with 0.8% PEG-18 Glyceryl Oleate/Cocoate (ANTIL 171, sold commercially by EVONIK Nutrition&Care GmbH) and about 0.4% NaCl, so as to achieve a viscosity of 3000-4000 mPas (Brookfield, spindle 2, 30 rpm).

38 g of these formulations are then introduced into a black plastic lid (height 1.9 cm; diameter 5.9 cm) and placed onto a black background within a light tent (manufacturer: Neewer, product number: 10026118, size: 40×40×40 cm). A digital camera (Canon EOS 605) equipped with a zoom lens (Canon EF-S 18-55 mm, 1:3.5-5.6) is fixed 32 cm above the upper edge of the lid. For homogeneous lighting of the sample, one external light source is set up to the right and one to the left of the light tent (eSmart ESL Photolamp: E27, diameter 72 mm, length 235 mm, 50 W, 3200 lumens, 5500K). The photos are taken at an aperture of f/5.5 and an exposure time of 1/100s, and zoom setting 55 mm. The photos are analysed using the program Photoshop CC 2015 Version 2015.0.1. For this purpose, a 60×60 mm image section is cut out of the middle of the photo and the histogram is read off. The luminance values thus obtained are evaluated and compared. The comparative substance used is the pearlescent agent TEGO Pearl N 300, sold commercially by EVONIK Nutrition&Care GmbH.

| | |
|---|---|
| Example 1.1 | 190 |
| Example 1.2 | 187 |
| Example 1.3 | 195 |
| Example 1.4 | 197 |
| Example 1.5 | 187 |
| Example 1.6 | 187 |
| TEGO Pearl N 300 (comparison) | 180 |

The invention claimed is:

1. A process for preparing an opaque composition, comprising:
   a) providing a starting composition comprising
      A) from 0.5 parts by weight to 15 parts by weight of disodium laureth sulfosuccinate,
      B) from 0.5 parts by weight to 15 parts by weight of Laureth-4,
      C) from 10 parts by weight to 30 parts by weight ethylene glycol distearate, and
      D) from 20 parts by weight to 85 parts by weight of water;
   b) stirring the starting composition at a temperature in a range from 60° C. to 100° C.; and
   c) cooling the starting composition to a temperature in a range from 5° C. to 55° C. to obtain the opaque composition, wherein the cooling is carried out at a cooling rate of from 0.1° C./min to 15° C./min,
   wherein said opaque composition has a turbidity value of 500 or more formazin nephelometric units, and
   wherein said opaque composition has a viscosity of 10 to 10,000 mPAs.

2. The process according to claim 1, wherein said opaque composition has a turbidity value of 1,000 or more formazin nephelometric units.

3. The process according to claim 1, wherein said opaque composition has a turbidity value of 1,200 or more formazin nephelometric units.

4. The process according to claim 1, wherein the starting composition of process step a) has a pH of from 4 to 7 at 20° C.

5. The process according to claim 1, wherein cooling to a temperature in a range of from 10° C. to 50° C. to obtain the opaque composition, and process step c) is carried out at a cooling rate of from 0.3° C./min/min to 5° C./min.

6. The process according to claim 1, wherein in process step c) the cooling is carried out at least partially by adding water to the starting composition, obtaining an opaque composition having a water content of 50% by weight to 85% by weight water, where the percentages by weight refer to the total composition.

7. The process according to claim 1, wherein the temperature of process step b) is 70° C. to 90° C., and the temperature of process step c) is 15° C. to 45° C.

8. The process according to claim 1, wherein process step c) is carried out at a cooling rate of from 0.3° C./min to 5° C./min.

9. The process according to claim 1, wherein the opaque composition has a viscosity of 100 to 7,000 mPA·s.

10. The process according to claim 1, wherein the opaque composition has a luminance of not less than 190.

11. The process according to claim 1, wherein the opaque composition has a turbidity value of not less than 1864.

12. The process according to claim 1, wherein the starting composition consists of the recited components A), B), C), and D).

13. The process according to claim 1, comprising 3 to 15 parts by weight of A) and 3 to 15 parts by weight of B).

14. A process for preparing opaque formulations comprising:
   a) providing a starting composition comprising
      A) from 3 parts by weight to 15 parts by weight of surfactant, wherein the surfactant consists of disodium laureth sulfosuccinate,
      B) from 3 parts by weight to 15 parts by weight of Laureth-4,
      C) from 10 parts by weight to 30 parts by weight ethylene glycol distearate, and
      D) from 20 parts by weight to 85 parts by weight water;
   b) stirring the starting composition at a temperature in a range from 60° C. to 100° C.,
   c) cooling to a temperature in a range from 15° C. to 45° C. to obtain the opaque composition, wherein the cooling is carried out at a cooling rate of from 0.1° C./min to 15° C./min; and
   d) blending the opaque composition with further components in a temperature range from 5° C. to 40° C. to obtain an opaque formulation,
   wherein said opaque composition has a turbidity value of 1,000 or more formazin nephelometric units, and wherein said opaque composition has a viscosity of 10 to 10,000 mPAs.

* * * * *